United States Patent
Takayama et al.

(10) Patent No.: US 7,071,229 B2
(45) Date of Patent: Jul. 4, 2006

(54) PROCESS FOR PRODUCING COROSOLIC ACID

(75) Inventors: Hiromitsu Takayama, Chiba-ken (JP); Mariko Kitajima, Chiba-ken (JP); Tomoko Ishizuka, Chiba-ken (JP); Shujiro Seo, Chiba-ken (JP)

(73) Assignee: Tokiwa, Phytochemical Co., Ltd., Sakura (JP)

( * ) Notice: Subject to any disclaimer, the term of this patent is extended or adjusted under 35 U.S.C. 154(b) by 0 days.

(21) Appl. No.: 10/866,733

(22) Filed: Jun. 15, 2004

(65) Prior Publication Data
US 2005/0020681 A1 Jan. 27, 2005

(30) Foreign Application Priority Data
Jun. 16, 2003 (JP) .............................. 2003-170130
Jun. 14, 2004 (JP) .............................. 2004-175695

(51) Int. Cl.
C07C 61/28 (2006.01)
A61K 31/20 (2006.01)

(52) U.S. Cl. ...................................... 514/559; 562/498
(58) Field of Classification Search ................ 514/557, 514/559; 562/498
See application file for complete search history.

(56) References Cited

U.S. PATENT DOCUMENTS
6,485,760 B1 * 11/2002 Matsuyama ................. 424/775

FOREIGN PATENT DOCUMENTS
EP       1 022 022 A1    7/2000
JP       2000-169384 A   6/2000
JP       2002-205949 A   7/2002

OTHER PUBLICATIONS
C. Murakami et al., Chem. Pharm. Bull. 41(12), pp. 2129-2131 (1993).
Z. Z. Liang et al., Planta Med., vol. 56, pp. 330-332 (1990).

* cited by examiner

Primary Examiner—Taylor Victor Oh
(74) Attorney, Agent, or Firm—Birch, Stewart, Kolasch & Birch, LLP

(57) ABSTRACT

This invention provides an improved process for producing corosolic acid starts from ursolic acid, which occurs in plants in relatively large amounts, the method comprising the steps of oxidizing the hydroxyl group at 3-position and utilizing the carbonyl group at 3-position to introduce a hydroxyl group stereospecifically into the 3-oxoursolic acid at the 2α-position adjacent to the hydroxyl group at 3-position.

4 Claims, 3 Drawing Sheets

PROCESS FOR PRODUCING COROSOLIC ACID

This Non-provisional application claims priority under 35 U.S.C. § 119(a) to Patent Application No(s). 2003-170130 and 2004-175695, filed in Japan on Jun. 16, 2003 and Jun. 14, 2004, respectively, the entire contents of which are hereby incorporated by reference.

BACKGROUND OF THE INVENTION

This invention relates to a process for producing corosolic acid (formula VIII) which is useful as an ingredient in medicines, cosmetics and health foods:

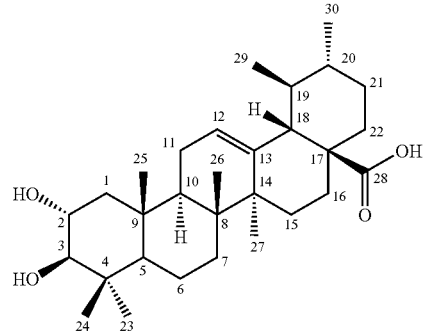

(VIII)

Corosolic acid is known to be contained in *Eriobotrya japonica* (loquat), *Lagerstroemia spesiosa* (banaba), *Rhabdosia japonicus* (Isodonis Herba), *Epilobium angustifolium* (fireweed), *Elliottia paniculata* (Hotsutsuji) and many other plants and it has been found to have pharmaceutical actions such as an anti-diabetic action and a blood glucose level lowering action (see JP 2002-205949 A and JP 2000-169384 A). However, a problem exists in that corosolic acid commonly occurs in a plant together with maslinic acid (formula VII), its position isomer with respect to methyl group being as follows:

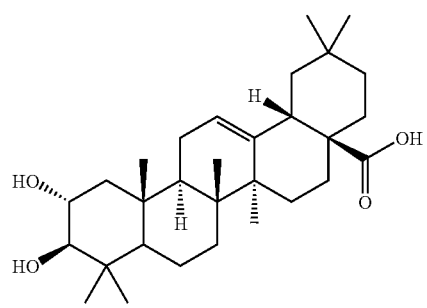

(VII)

which makes it difficult to obtain corosolic acid in pure form on an industrial scale, thus limiting its medical usability. In small-scale production in the laboratory, corosolic acid is prepared by chromatographic isolation from plant extracts (see, for example, Chem. Pharm. Bull., vol. 41, p. 2129, 1993 and Planta Med., vol. 56, p. 330, 1990). However, in using this method problems of low corosolic acid content in a plant and low efficiency in chromatographic separation are encountered, and thus it is not a practical method in terms of cost-effectiveness; and is not suitable for use on an industrial scale.

SUMMARY OF THE INVENTION

It is therefore an object of the present invention to provide a process by which corosolic acid can be produced on an industrial scale, cost-effectively at a high yield.

The present inventors have made intensive studies with a view to synthesizing corosolic acid on an industrial scale, cost-effectively, and as a consequence discovered a method for synthesizing corosolic acid from ursolic acid (formula IX) which occurs in plants in relatively large amounts:

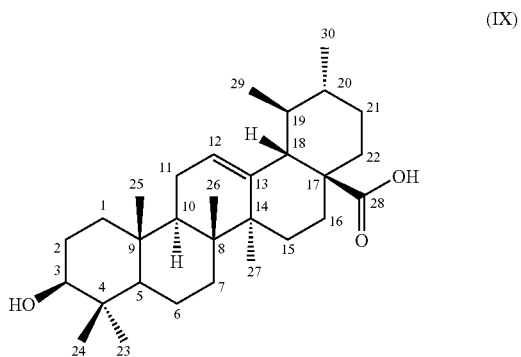

(IX)

More specifically, the present inventors have discovered a method for producing corosolic acid by introducing a hydroxyl group stereospecifically into ursolic acid at the 2α-position adjacent to the hydroxyl group at 3-position. The present invention has been accomplished on the basis of this discovery.

Thus, according to one aspect of the invention, there is provided a process for producing corosolic acid or a corosolic acid ester, which comprises the steps of:

a) oxidizing a compound of formula III:

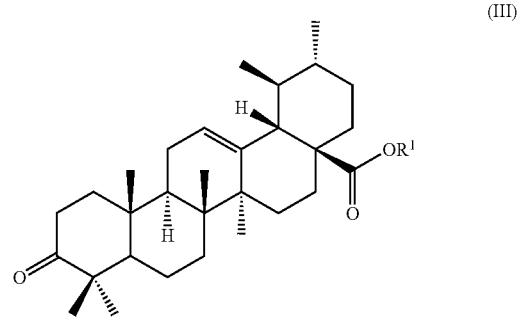

(III)

[where $R^1$ is a hydrogen atom or a $C_1$–$C_6$ alkyl] to a compound of formula IV:

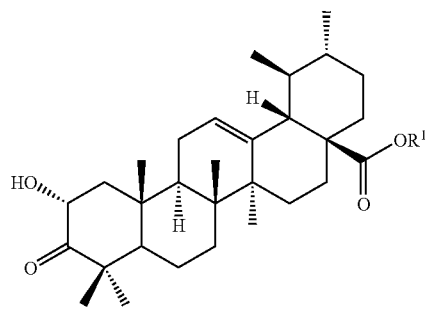
(IV)

[where $R^1$ is a hydrogen atom or a $C_1$–$C_6$ alkyl]; and
b) reducing the compound of formula IV to corosolic acid of formula I:

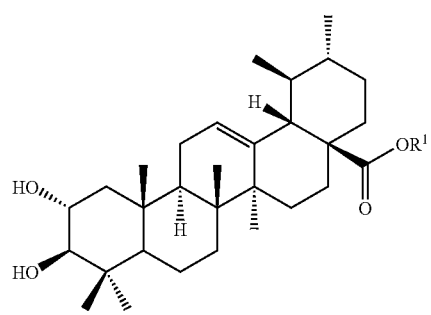
(I)

[where $R^1$ is a hydrogen atom or a $C_1$–$C_6$ alkyl] or a corosolic acid ester.

According to another aspect of the invention, there is provided a process for producing corosolic acid or a corosolic acid ester, which comprises the steps of:
a) oxidizing a compound of formula II:

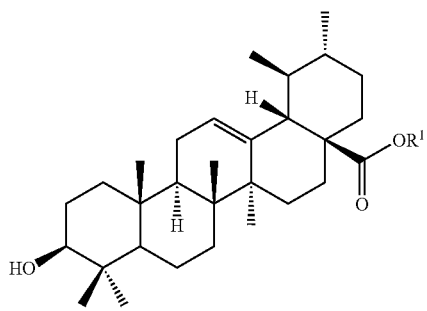
(II)

[where $R^1$ is a hydrogen atom or a $C_1$–$C_6$ alkyl] to a compound of formula III;
b) oxidizing the compound of formula III to a compound of formula IV; and
c) reducing the compound of formula IV to corosolic acid of formula I or a corosolic acid ester.

In the above-mentioned processes, $R^1$ is preferably a hydrogen atom.

According to still another aspect of the invention, there is provided a process which is a modification of the above-mentioned processes wherein $R^1$ is a $C_1$–$C_6$ alkyl and which further includes the step of:
d) hydrolyzing the compound of formula I:

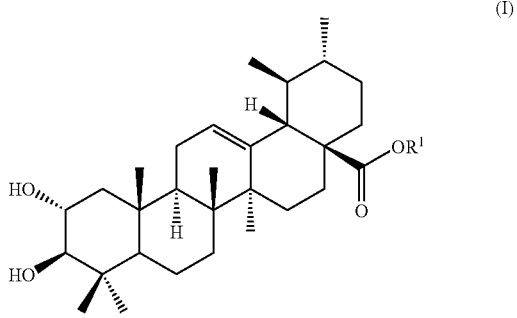
(I)

[where $R^1$ is a $C_1$–$C_6$ alkyl] to a compound of formula VIII:

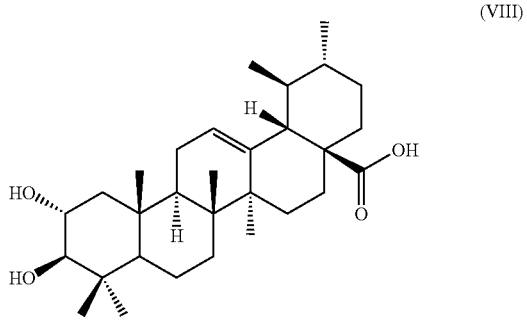
(VIII)

The $C_1$–$C_6$ alkyl is a linear or branched alkyl group having 1–6 carbon atoms, as exemplified by methyl, ethyl, n-propyl, i-propyl, n-butyl, s-butyl, i-butyl, t-butyl, n-pentyl, 3-methylbutyl, 2-methylbutyl, 1-methylbutyl, 1-ethylpropyl, n-hexyl, 4-methylpentyl, 3-methylpentyl, 2-methylpentyl, 1-methylpentyl, 3-ethylbutyl, 2-ethylbutyl, etc. Preferred $C_1$–$C_6$ alkyls include methyl, ethyl, i-propyl, etc.

According to yet another aspect of the invention, there are also provided pharmaceutical compositions as well as foods and beverages that contain corosolic acid or corosolic acid esters produced by any one of the processes described above. The pharmaceutical compositions may be used to prevent or treat diabetes mellitus or control blood glucose level.

DETAILED DESCRIPTION OF THE INVENTION

Figure 1:
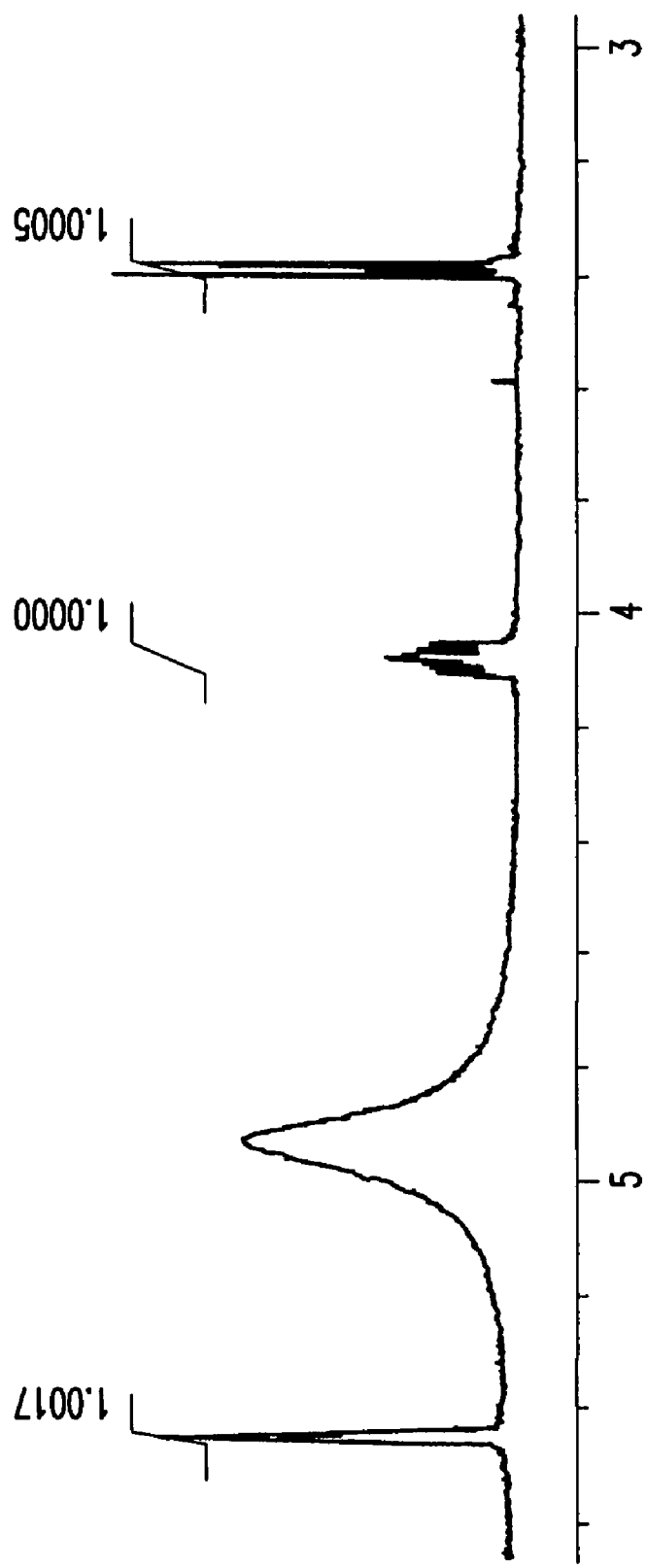
FIG. 1 shows a $^1$H-NMR spectrum for corosolic acid (proton at 2β- and 3α-positions; 500 MHz; solvent, Py-$D_5$)

In order to introduce a hydroxyl group into ursolic acid at 2-position stereoselectively, the process of the invention for producing corosolic acid comprises the steps of converting ursolic acid to 3-oxoursolic acid using a suitable oxidizing agent in a solvent, introducing a hydroxyl group into the 3-oxoursolic acid at the 2α-position adjacent the carbonyl group, then performing a reaction for reducing the 3-oxo group in the 2α-hydroxy-3-oxoursolic acid to a 3β-hydroxyl group using a suitable reducing agent in a solvent.

Urosolic acid as the starting material is typically a purified extract from plants containing ursolic acid. Alternatively, 3-oxoursolic acid or commercial grades of ursolic acid may be employed. If desired, starting from ester derivatives of ursolic acid or 3-oxoursolic acid, the above-mentioned reactions may be carried out and the ester group then subjected to hydrolysis.

The following scheme 1 is used for oxidizing the hydroxyl group at 3-position of ursolic acid:

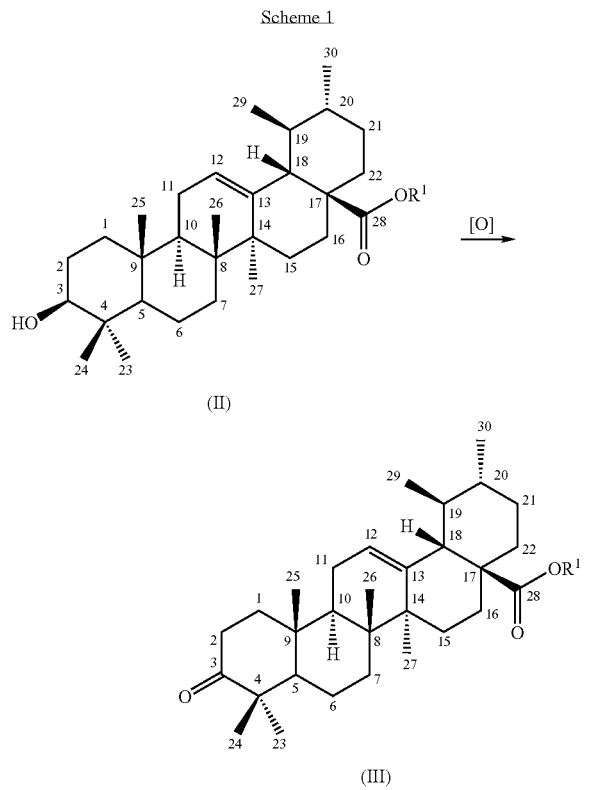

In scheme 1, $R^1$ is a hydrogen atom or a $C_1$–$C_6$ alkyl. Oxidizing agents common in the art of interest may be employed in the oxidizing step without any particular limitation. Examples are hypervalent iodine reagents such as a Dess-Martin reagent, DMSO-oxalyl chloride or DMSO-trifluoroacetic acid anhydride (Swern oxidation), DMSO-DCC (Pfitzner-Moffat oxidation), DMSO-SO₃ pyridine complex (Parikh-Doering oxidation), DMSO-chlorine or DMSO-N-chlorosuccinimide (Corey-Kim oxidation), aluminum alkoxides (aluminum isopropoxide and aluminum tert-butoxide), etc. In the step under consideration, oxidizing with pyridinium chlorochromate or Dess-Martin reagent or oxidizing by Swern oxidation is particularly preferred. In the oxidizing step, the oxidizing agent can be used in moles 1.0–1.5 times, preferably 1.0–1.2 times, the mole of the compound of formula (II). Any solvents can be used in the oxidizing step without particular limitation as long as they are inert to the reaction. Exemplary solvents are methylene chloride, chloroform, ether and mixtures thereof, with methylene chloride being particularly preferred. The reaction temperature for the oxidizing step is typically in the range from 0° C. to room temperature, preferably between 0° C. and 25° C.

The method of introducing a hydroxyl group into formula (III) at the 2α-position of ketone is not limited in any particular way; to give an example, formula (III) is treated with a commonly known silylating agent so it is converted to silyl enolate, which is oxidized with an organic peracid, etc., and the reaction mixture is treated with an acid, etc. to give a 2α-hydroxy-3-oxo derivative (scheme 2):

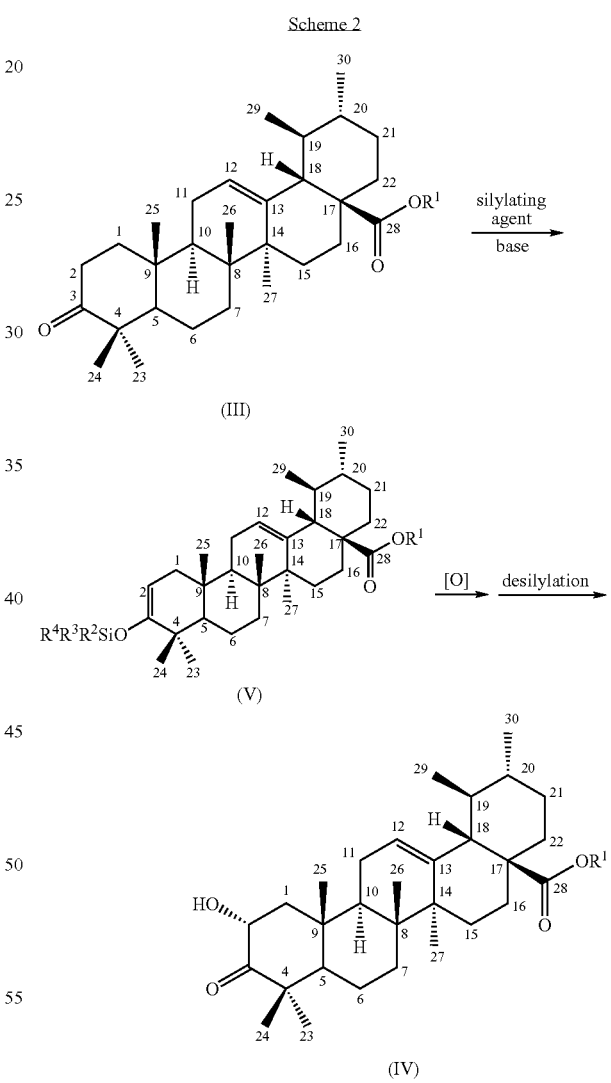

In scheme 2, $R^1$ is a hydrogen atom or a $C_1$–$C_6$ alkyl, and $R^2$, $R^3$ and $R^4$ are each independently selected from among $C_1$–$C_6$ alkyls and phenyl. Examples of the silylating agent used to obtain the silyl enolate of formula (V) include BSA (N,O-bis(trimethylsilyl)acetamide), BSU (N,N'-bis(trimethylsilyl)urea) or triethylamine or other tertiary amines (e.g. diisopropylethylamine or DBU) or aromatic amines (e.g. pyridine, 2,6-dimethylpyridine or 4-dimethylaminopyridine), which may be used in combination with trimethylsilyl trifluoromethanesulfonate or chlorosilanes (e.g. trimethylsilyl chloride or t-butyldimethylsilyl chloride). Preferred silylating agents are trimethylsilyl trifluoromethanesulfonate, t-butyldimethylsilyl trifluoromethanesulfonate and BSA. In the silylating step, the silylating agent can be used in moles 3–6 times, preferably 4–5 times, the mole of the compound of formula (III). Any solvents can be used in the silylating step without particular limitation as long as they are inert to the reaction. Exemplary solvents are methylene chloride, chloroform, ether and mixtures thereof, with methylene chloride being particularly preferred. The reaction temperature for the silylating step is typically in the range from −78° C. to room temperature, preferably between −78° C. and 0° C.

In the step of oxidizing the compound of formula (V), various compounds can be used as the oxidizing agent and they include organic peracids such as metachloroperbenzoic acid, perbenzoic acid, monoperoxyphthalic acid, performic acid, peracetic acid, trifluoroperacetic acid, as well as osmic acid and derivatives thereof. In this oxidizing step, the oxidizing agent can be used in moles 1.0–1.5 times, preferably 1.1–1.2 times, the mole of the compound of formula (V). Any solvents can be used in the oxidizing step without particular limitation as long as they are inert to the reaction. Exemplary solvents are methylene chloride, chloroform, ether and mixtures thereof, with methylene chloride being particularly preferred. The reaction temperature for this oxidizing step is typically in the range from −25° C. to room temperature, preferably between −20° C. and 0C.

Transformation from the above-described reaction intermediate to the compound of formula (IV) involving desilylation can be performed by treatment with inorganic acids such as hydrochloric acid and sulfuric acid, or fluorides such as tetrabutylammonium fluoride and potassium fluoride.

Another method that can used to introduce a hydroxyl group into the compound of formula (III) at the 2α-position is expressed below by scheme 3:

Scheme 3

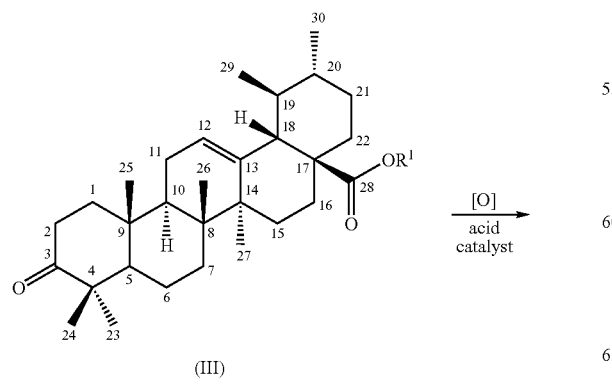

(III)

-continued

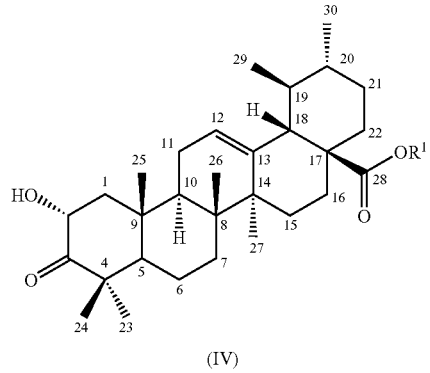

(IV)

In scheme 3, $R^1$ is a hydrogen atom or a $C_1$–$C_6$ alkyl. The oxidizing agent that can be used in the oxidizing step under consideration is an organic peracid such as m-chloroperbenzoic acid, perbenzoic acid, monoperoxyphthalic acid, performic acid, peracetic acid or trifluoroperacetic acid. The catalyst that can be used in the step of interest is an inorganic acid such as sulfuric acid or hydrochloric acid. In this oxidizing step, the oxidizing agent can be used in moles 1.0–2.0 times, preferably 1.0–1.3 times, the mole of the compound of formula (III). Any solvents can be used in the oxidizing step without particular limitation as long as they are inert to the reaction. Exemplary solvents are methylene chloride, chloroform, ether and mixtures thereof with methanol or ethanol, with a mixture of methylene chloride and methanol being particularly preferred. The reaction temperature for the oxidizing step is typically in the range from −78° C. to room temperature, preferably between −20° C. and 0° C.

The step of reducing formula (VI) is shown below by scheme 4:

Scheme 4

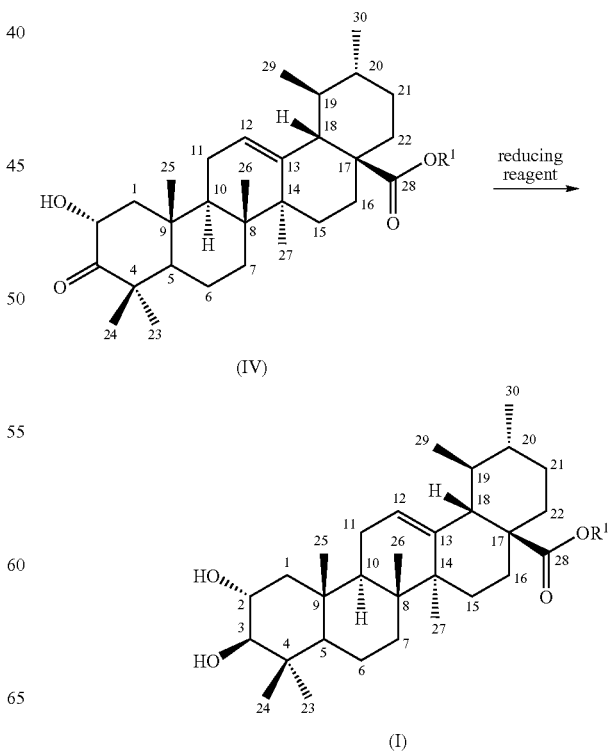

In scheme 4, $R^1$ is a hydrogen atom or a $C_1$–$C_6$ alkyl. The reducing agent to be used in the step under consideration to reduce the 3-oxo group is not limited in any particular way and examples include $NaBH_4$, $[(CH_3)_2CHCH_2]_2AlH$, $LiAlH(OR_6)_3$ ($R^6$ is a $C_1$–$C_6$ alkyl), $NaBH_3CN$, $LiBH_3CN$, $Zn(BH_4)_2$, etc. Any solvents can be used in the reducing step without particular limitation as long as they are inert to the reaction. The reaction temperature for the reducing step is typically in the range from −50° C. to room temperature, preferably between −20° C. and 20° C.

According to one aspect of the invention, there is provided a process for producing corosolic acid by carrying out the above-described reactions starting from an ester derivative of ursolic acid or 3-oxoursolic acid and hydrolyzing the corosolic acid ester obtained (scheme 5):

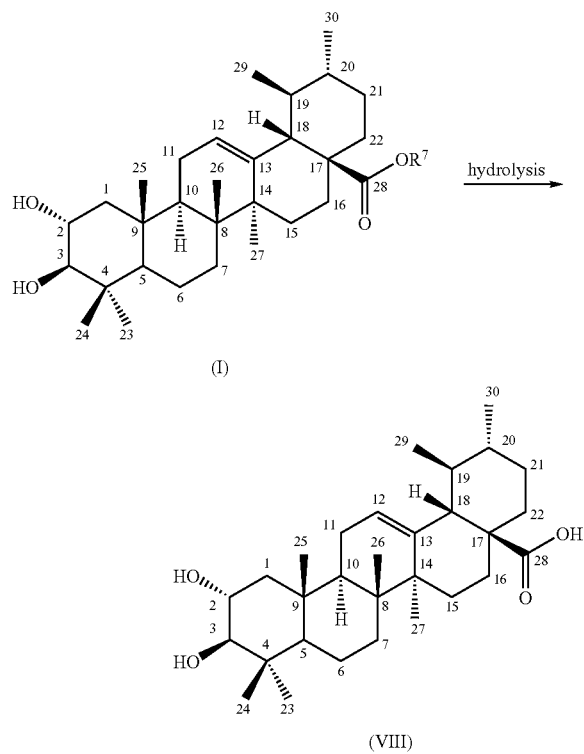

In scheme 5, $R^7$ is a $C_1$–$C_6$ alkyl. Hydrolysis in the step under consideration can be performed by any methods common in the art of interest without particular limitation; examples include alkali hydrolysis using sodium hydroxide, potassium hydroxide, etc. and acid hydrolysis using hydrochloric acid, sulfuric acid, etc. Another method that can be employed is the use of a Lewis acid such as aluminum bromide or aluminum chloride. Any solvents can be used in the hydrolyzing step without particular limitation as long as they are inert to the reaction.

The synthesis intermediate that is obtained in the processes of the invention can be used in the next step without being subjected to any special purification procedures; if desired, it may be purified by methods commonly employed in the art before it is used in the next step. Corosolic acid and derivatives thereof that are obtained as the end product can also be purified by methods common in the art of interest. Exemplary methods of purification that may be employed in the invention include various chromatographic techniques and recrystallization. The solvents that can be used in recrystallization include organic solvents such as chloroform, dichloromethane, benzene, toluene, xylene, ethyl acetate, diethyl ether, methyl ethyl ether, diisopropyl ether, acetone methyl ethyl ketone, methanol, ethanol, 2-propanol, DMSO, dioxane and tetrahydrofuran, as well as water and mixtures thereof.

In the present specification, "α" refers to the configuration of a bond directed into the paper on which the structural formula is written whereas "β" refers to the configuration of a bond directed toward the viewer from the paper on which the structural formula is written.

The structure and purity of corosolic acid can be verified by $^1$H-NMR, $^{13}$C-NMR and HPLC.

The corosolic acid or corosolic acid esters prepared by the processes described above can be used as an active ingredient in pharmaceutical compositions. Such pharmaceutical compositions may be either drugs for oral administration or drugs for parenteral administration. In the former case, the compositions may be administered as soft capsules, hard capsules, tablets, granules, subtilized granules or powders. Methods for parenteral administration include administration into local tissue, intradermal injection, subcutaneous injection, intramuscular injection and intravenous injection, as well as topical application, spray, etc. The pharmaceutical compositions of the invention can contain various commonly employed ingredients; for example, they can contain one or more pharmaceutically acceptable additives including excipients, diluents, wetting agents, emulsifiers, dispersants, auxiliary agents, antiseptics, buffers, binders, stabilizers, etc. The dosage form for topical application of the pharmaceutical compositions according to the invention is not limited in any particular way and examples include ointments, creams, lotions and sprays.

The dose of corosolic acid can be chosen for use at any suitable level, taking into account such factors as physique, age and physical condition of the patient, severity of the disease and the lapse of time from its onset. Typically, it is used in a dose of 1–5000 mg/day, preferably 1–500 mg/day, in an adult.

The corosolic acid or corosolic acid esters prepared by the processes of the invention can be used as an ingredient or ingredients in quasi-drugs, cosmetics, beverages, foods, etc. or as food additives. By so doing, corosolic acid can be taken into the body in everyday life on a continuous basis, making it possible to control blood glucose level, provide an effective treatment of diabetes mellitus and prevent the manifestation of diabetes mellitus. Cases of using corosolic acid as an ingredient in foods and beverages include functional foods, health foods, common foods (e.g. juice, cookies and processed food) and dietary supplements (nutrition drinks), etc. that are capable of preventing and/or treating diabetes mellitus or controlling the blood glucose level.

According to the processes of the invention, corosolic acid or corosolic acid esters can be efficiently produced in high yield at low cost.

The following examples are provided for further illustrating the present invention but are in no way to be taken as limiting. Various changes and modifications can be made by the skilled artisan and encompassed in the present invention.

EXAMPLE 1

Pyridinium chlorochromate (431 mg) was added to a solution of ursolic acid (456 mg) in methylene chloride and the mixture was stirred at room temperature for 6 hours. The reaction mixture was filtered through Celite. The filtrate was concentrated at reduced pressure and the residue was purified by silica gel column chromatography and crystallized from a liquid mixture of ethyl acetate and hexane to give 3-oxoursolic acid (360 mg, 79% in yield).

EXAMPLE 2

To a solution of ursolic acid (228 mg) in methylene chloride, 1,1,1-tris(acetyloxy)-1,1-dihydro-1,2-benziodoxol-3-(1H)-one (Dess-Martin reagent, 254 mg) was added and the mixture was stirred at room temperature for 1 hour. The reaction mixture was poured into water and extracted with chloroform. The organic layer obtained was dried on magnesium sulfate and then concentrated at reduced pressure. The resulting residue was crystallized from a liquid mixture of ethyl acetate and hexane to give 3-oxoursolic acid (193 mg, 85% in yield).

EXAMPLE 3

A solution of DMSO (300 μL) in anhydrous methylene chloride was added slowly dropwise to a stirred solution of oxalyl chloride (185 μL) in anhydrous methylene chloride at −50° C. The reaction mixture was stirred for 20 minutes and then a solution of ursolic acid (456 mg) in anhydrous methylene chloride was added slowly dropwise. Following continued stirring for 20 minutes at the same temperature, triethylamine (830 μL) was finally added dropwise and the mixture was stirred as such for 10 minutes. Stirring was continued for 2 more hours with the reaction temperature gradually being elevated to room temperature. The reaction mixture was poured into 5% aqueous hydrochloric acid and after separating the organic layer, the aqueous layer was extracted with methylene chloride. The combined organic layers were dried on magnesium sulfate and concentrated at reduced pressure. The resulting residue was crystallized from a liquid mixture of ethyl acetate and hexane to give 3-oxoursolic acid (363 mg, 80% in yield).

EXAMPLE 4

A solution of anhydrous trifluoroacetic acid (300 μL) in anhydrous methylene chloride was added slowly dropwise to a stirred solution of DMSO (300 μL) in anhydrous methylene chloride at −25° C. The reaction mixture was stirred at the same temperature for 10 minutes and then a solution of ursolic acid (456 mg) in anhydrous methylene chloride was added slowly dropwise. Following continued stirring for 20 minutes at the same temperature, triethylamine (830 μL) was finally added dropwise and the mixture was stirred as such for 15 minutes. The stirring was continued for 1 more hour with the reaction temperature gradually being elevated to room temperature. The reaction mixture was poured into 5% aqueous hydrochloric acid and after separating the organic layer, the aqueous layer was extracted with methylene chloride. The combined organic layers were dried on magnesium sulfate and concentrated at reduced pressure. The resulting residue was crystallized from a liquid mixture of ethyl acetate and hexane to give 3-oxoursolic acid (318 mg, 70% in yield). $^1$H-NMR (500 MHz, CDCl$_3$) δ5.28 (1H, t, J=3.5 Hz), 2.54 (1H, ddd, J=7.6, 10.7, 16.1 Hz), 2.38 (1H, ddd, J=3.7, 6.7, 15.9 Hz), 2.21 (1H, d, J=11.3 Hz), 1.10 (3H, s), 1.09 (3H, s), 1.06 (3H, s), 1.04 (3H, s), 0.85 (3H, s), 0.95 (3H, d, J=6.1 Hz ), 0.87 (3H, d, J=6.7 Hz).

EXAMPLE 5

Triethylamine (in 10 mole equivalents to the substrate) and trimethylsilyl trifluoromethanesulfonate (in 5 mole equivalents to the substrate) were successively added to a solution of 3-oxoursolic acid (227 mg) in methylene chloride at low temperature and the mixture was stirred for 1 hour. The reaction mixture was poured into iced water and extracted with chloroform. The organic layer obtained was dried on magnesium sulfate and concentrated at reduced pressure. The resulting residue was dissolved in methylene chloride and a solution of metachloroperbenzoic acid (in 1.2 mole equivalents to the substrate) in methylene chloride was added under cooling with ice. After stirring at the same temperature for 1 hour, the reaction mixture was poured into 5% aqueous hydrochloric acid and extracted with chloroform. The organic layer obtained was dried on magnesium sulfate and concentrated at reduced pressure. The residue was crystallized from ethyl acetate to give 2α-hydroxy-3-oxoursolic acid (190 mg, 81% in yield).

EXAMPLE 6

A methanol solution (10 mL) containing a catalytic amount (ca. 0.05% v/v) of sulfuric acid was added to a solution of 3-oxoursolic acid (227 mg) in methylene chloride (5 mL); then, metachloroperbenzoic acid (in 1.3 mole equivalents to the substrate) was added and the mixture was stirred at room temperature for several hours in the absence of light. The reaction mixture was diluted with methylene chloride and washed with water, 5% aqueous sodium hydrogensulfite, water, saturated aqueous sodium hydrogencarbonate and water in that order. The organic layers were dried on magnesium sulfate and concentrated at reduced pressure. The resulting residue was crystallized from ethyl acetate to give 2α-hydroxy-3-oxourosolic acid (141 mg, 60% in yield). $^1$H-NMR (500 MHz, CDCl$_3$) δ5.25 (1H, br-s), 4.55 (1H, dd, J=6.6, 12.7 Hz), 2.44 (1H, dd, J=6.6, 12.6 Hz), 2.20 (1H, d, J=11.3 Hz), 1.28 (3H, s), 1.16 (3H, s), 1.10 (3H, s), 1.06 (3H, s), 0.83 (3H, s), 0.95 (3H, d, J=7.4 Hz), 0.85 (3H, d, J=6.4 Hz).

EXAMPLE 7

To a solution of 2α-hydroxy-3-oxoursolic acid (100 mg) in ethanol, NaBH$_4$ (in 5 mole equivalents to the substrate) was added gradually under cooling with ice. The mixture was stirred at the same temperature for 30 minutes and thereafter poured carefully into cold 5% aqueous hydrochloric acid and extracted with 5% methanol containing chloroform. The organic layer obtained was dried on magnesium sulfate and concentrated at reduced pressure. The residue was crystallized from alcohol to give corosolic acid (85 mg, 85% in yield).

$^1$H-NMR (500 MHz, Py-D$_5$) δ5.45 (1H, br-s), 4.07 (1H, dt, J=6.7, 9.5 Hz), 3.39 (1H, d, J=9.5 Hz), 2.61 (1H, d, J=11.3 Hz), 2.22 (1H, dd, J=12.8, 4.6 Hz), 1.26 (3H, s), 1.20 (3H, s), 1.07 (3H, s), 1.04 (3H, s), 0.97 (3H, s), 0.97 (3H, d, J=7.4 Hz), 0.92 (3H, d, J=6.4 Hz).

Figure 2:
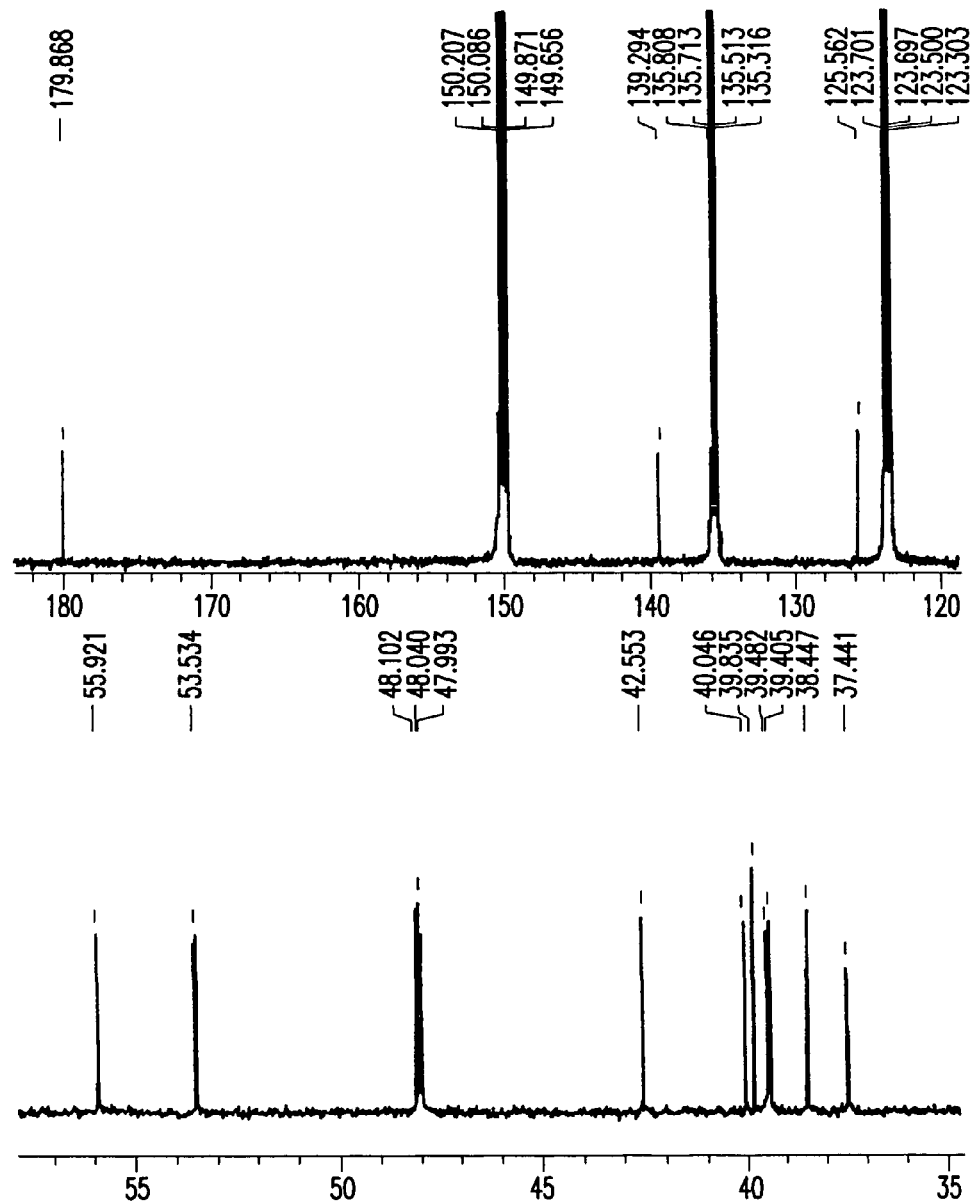
FIG. 2 shows a $^{13}$C-NMR spectrum for corosolic acid (125 MHz; solvent, Py-$D_5$)
Figure 3:
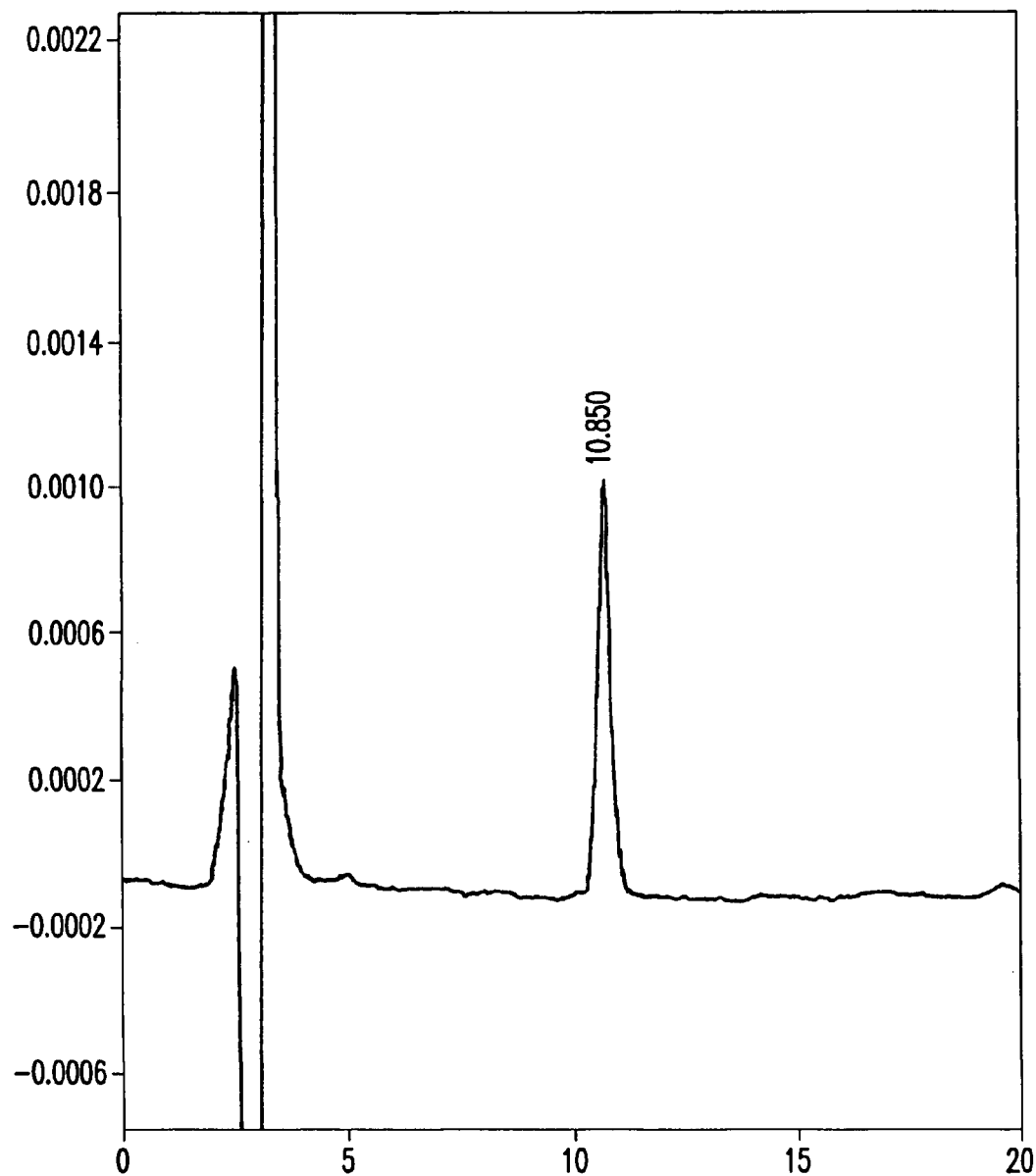
FIG. 3 shows an HPLC spectrum for corosolic acid (column, CAPCELL PACK C18; mobile phase, $CH_3CN$/$H_2O$/TFA=65/35/0.1; detection, UV 250 nm; injected dose, 10 μl (0.59 mg)).

The structure of the obtained corosolic acid was verified by taking $^1$H-NMR spectrum (500 MHz; solvent, Py-D$_5$) and $^{13}$C-NMR spectrum (125 MHz; solvent, Py-D$_5$). The peaks in the $^{13}$C-NMR spectrum (see FIG. 2) are assigned as follows:

Corosolic acid

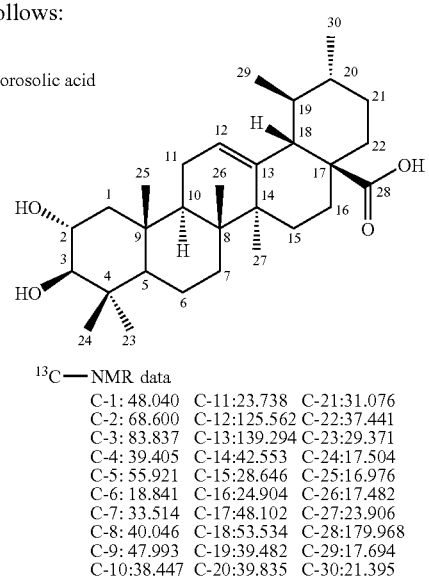

$^{13}$C—NMR data

C-1: 48.040   C-11:23.738   C-21:31.076
C-2: 68.600   C-12:125.562  C-22:37.441
C-3: 83.837   C-13:139.294  C-23:29.371
C-4: 39.405   C-14:42.553   C-24:17.504
C-5: 55.921   C-15:28.646   C-25:16.976
C-6: 18.841   C-16:24.904   C-26:17.482
C-7: 33.514   C-17:48.102   C-27:23.906
C-8: 40.046   C-18:53.534   C-28:179.968
C-9: 47.993   C-19:39.482   C-29:17.694
C-10:38.447   C-20:39.835   C-30:21.395

The $^1$H-NMR spectrum (see FIG. 1) showed no presence of epimers of corosolic acid at 2- and 3-positions (2β-hydroxy form and 3α-hydroxy form).

What is claimed is:

1. A process for producing corosolic acid or a corosolic acid ester, which comprises the steps of:

a) oxidizing a compound of formula III:

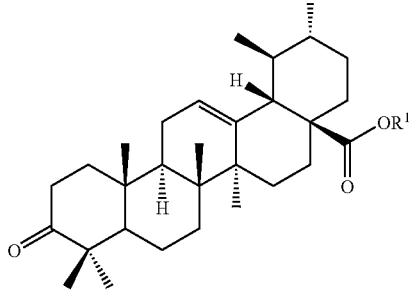

where $R^1$ is a hydrogen atom or a $C_1$–$C_6$ alkyl in a solvent to a compound of formula IV:

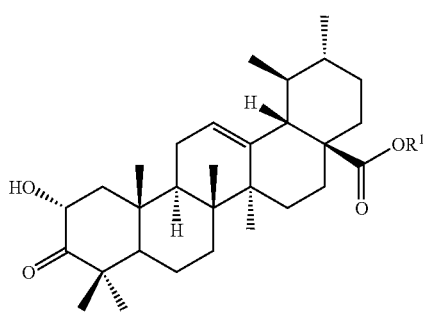

where $R^1$ is a hydrogen atom or a $C_1$–$C_6$ alkyl; and b) reducing the compound of formula IV, in a solvent at a temperature in the range from −50° C. to room temperature, to corosolic acid of formula I:

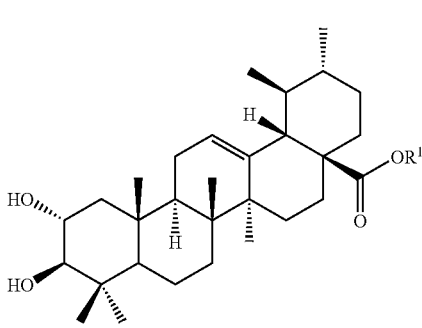

where $R^1$ is a hydrogen atom or a $C_1$–$C_6$ alkyl or a corosolic acid ester.

2. The process according to claim 1, wherein the step of oxidizing a compound of formula II:

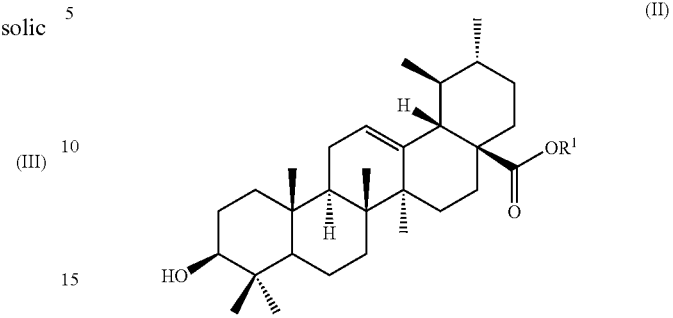

where $R^1$ is a hydrogen atom or a $C_1$–$C_6$ alkyl, in a solvent at a temperature in the range from 0° C. to room temperature, to a compound of formula III is further included before step a).

3. The process according to claim 1 or 2, wherein $R^1$ is a hydrogen atom.

4. The process according to claim 1 or 2, wherein $R^1$ is a $C_1$–$C_6$ alkyl and which further includes step d) of hydrolyzing the compound of formula I:

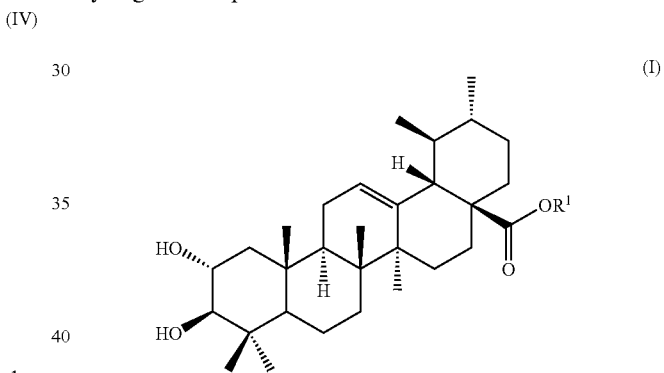

where $R^1$ is a $C_1$–$C_6$ alkyl, by alkali hydrolysis or acid hydrolysis in a solvent, to corosolic acid of formula VIII:

* * * * *

UNITED STATES PATENT AND TRADEMARK OFFICE
CERTIFICATE OF CORRECTION

PATENT NO. : 7,071,229 B2  
APPLICATION NO. : 10/866733  
DATED : July 4, 2006  
INVENTOR(S) : Hiromitsu Takayama et al.

It is certified that error appears in the above-identified patent and that said Letters Patent is hereby corrected as shown below:

On the Title page, Item (73) should read:

-- Item (73) Assignee: Tokiwa Phytochemical Co., Ltd., Sakura (JP) --

Signed and Sealed this

Sixteenth Day of October, 2007

JON W. DUDAS  
*Director of the United States Patent and Trademark Office*